(12) United States Patent
Nishimura et al.

(10) Patent No.: US 6,544,511 B2
(45) Date of Patent: Apr. 8, 2003

(54) PLANT DISEASE CONTROL AGENT

(75) Inventors: Tomio Nishimura, Mie (JP); Hitoshi Kunoh, 31-113, Shiratsukacho, Tsu-shi, Mie 514-0101 (JP); Tamotsu Furumai, Kanagawa (JP); Yasuhiro Igarashi, Toyama (JP); Yukio Sato, Toyama (JP); Masafumi Shimizu, Tottori (JP)

(73) Assignees: Akatsuka Orchid Co., Ltd., Tsu (JP); Hitoshi Kunoh, Tsu (JP)

( * ) Notice: Subject to any disclaimer, the term of this patent is extended or adjusted under 35 U.S.C. 154(b) by 0 days.

(21) Appl. No.: 09/801,651

(22) Filed: Mar. 9, 2001

(65) Prior Publication Data

US 2001/0031258 A1 Oct. 18, 2001

(30) Foreign Application Priority Data

Mar. 9, 2000 (JP) ........................................ 2000-065511
Jan. 17, 2001 (JP) ........................................ 2001-009323

(51) Int. Cl.$^7$ ..................... A01N 63/000; C12N 1/22
(52) U.S. Cl. .......................... 424/93.43; 435/252.35
(58) Field of Search ................... 424/93.43; 435/252.35

(56) References Cited

U.S. PATENT DOCUMENTS 4,051,255 A * 9/1977 Davidson
4,164,405 A * 8/1979 Pinckard
5,602,111 A * 2/1997 Misaki et al.

OTHER PUBLICATIONS

Orekhov, D.A. Mikologiya i Fitopatologiya (1974), vol. 8 (4): 361–363. The biological method of controlling the root fungus—Fomitopsis annosa (Fr.) Karst.*

* cited by examiner

Primary Examiner—Christopher R. Tate
Assistant Examiner—Michele C. Flood
(74) Attorney, Agent, or Firm—Birch, Stewart, Kolasch & Birch, LLP

(57) ABSTRACT

A disease control agent and a phytoalexin inducing agent, comprising Streptomyces sp. R-5 as an active ingredient are disclosed. Disease-resistant plants may be produced by inoculating plants with the disclosed Streptomyces sp. R-5. The disease control agent and a phytoalexin inducing agent are further useful in that they have low toxicity to humans and cause no environmental contamination.

10 Claims, 11 Drawing Sheets

(4 of 11 Drawing Sheet(s) Filed in Color)

Days after treated with R-5 strain

PLANT DISEASE CONTROL AGENT

BACKGROUND OF THE INVENTION

1. Field of the Invention

The present invention relates to Streptomyces sp. R-5; a plant disease control agent comprising the strain as an active ingredient; a method for producing disease-resistant plants characterized by inoculating the strain to the plants; and a phytoalexin inducer agent comprising the strain as an active ingredient.

2. Prior Art

Ornamental plants have been grown in many ways such as soil culture in plastic green house, pot culture, water culture, gravel culture and rock wool culture, or open culture. However in such cultures, ornamental plants infected with pathogenic microorganisms often lose their commercial value. Various methods have been devised to control such disease damages. For example, methods employed in soil culture include sterilization of plants with agricultural chemicals, such as TPN (tetrachloroisophthalonitrile), captan, eclomezol, metalaxyl, mepronil, and PCNB (pentachloronitrobenzene) agent; disinfection of plants with solar heat wherein the soil surface layer where plant pathogenic microorganisms are present is covered by a black vinyl sheet; and fumigation of the deep ground portion of soil using agricultural chemicals, such as methyl bromide and chlorpicrate, which generate toxic gas. Methods tried in water culture, gravel culture, and rock wool culture, include disinfection of the entire installation using formalin or sodium hypochlorite or mixing culture fluid with eclomezol or TPN agent.

Currently, ornamental plants, such as rhododendron and mountain laurel, members of Ericaceae family, are cultivated as follows. Seedlings of ornamental plants are raised in media in glass or plastic containers, transplanted onto a substrate such as soil, vermiculite or sphagnum, then acclimatized to an outdoor environment. During these cultivation steps, seedlings are raised on artificial media under sterile conditions so that only a few of them suffer from plant pathogenic microorganisms. Immediately after acclimation starts, however, plants can become afflicted by plant pathogenic microorganisms present around the plants. In some cases entire seedlings can wilt or be killed. To avoid this, after seedlings are taken out of their containers, they are transplanted into nursery beds consisting of soil or vermiculite and sphagnum, and agricultural chemicals such as metalaxyl, captan, validamycin, and TPN are applied to the seedlings. Even after seedlings are planted in fields, benomyl, TPN, maneb, mancozeb, metalaxyl and the like are often applied to the seedlings for disease control. Cultivation of ornamental plants using such tissue culture seedlings is conducted in Southeast Asia. For example in Thailand, large amounts of agricultural chemicals are used for disease control. There is concern that potted plants imported and brought into households from such countries can affect the human body with volatile agricultural chemicals.

Measures for plant disease control, independent of agricultural chemicals, such as manuring practice, raising resistant varieties, and eliminating a source of secondary infection have been tested. However, there is a limit to the efficacy of such indirect measures. Currently, there is no known effective method other than treatment with agricultural chemicals, and elimination or incineration of infected plants. Gas used for disinfecting soil, such as methyl bromide and chlorpicrate is toxic to the human body and tends to cause air pollution. Recently, strict regulations have reduced the toxicity of agricultural chemicals, but on the other hand, have led to an increase in the number of times that such agricultural chemicals are used. There is a danger that, as a result this will lead to environmental contamination, such as soil and air pollution, which in turn is linked to serious problems, such as hormone-disrupting substances that adversely affect future generations. There is a fear that repetitive use of agricultural chemicals may induce pathogenic microorganisms to become resistant to the chemicals. Accordingly, safe methods for controlling plant diseases, which have low toxicity to humans and cause no environmental contamination, are required.

SUMMARY OF THE INVENTION

The present invention provides a biotic pesticide having low toxicity to humans and causing no environmental contamination. That is, the present invention provides Streptomyces sp. R-5; a plant disease control agent comprising this strain as an active ingredient; a method for producing a disease-resistant plant comprising inoculating the strain to plants; and a phytoalexin inducer agent comprising the strain as an active ingredient.

The inventors have succeeded in producing a disease-resistant plant by inoculation of Streptomyces sp. R-5 isolated from rhododendron as a result of diligent research on the above problems.

The present invention relates to a plant disease control agent comprising Streptomyces spp. [for example, Streptomyces sp. R-5(FERM BP-7179)] as an active ingredient. R-5 (deposit number: FERM BP-7179) is deposited under the Budapest Treaty at National Institute of Bioscience and Human-Technology Agency of Industrial Science and Technology, at 1-3, Higashi 1-chome, Tsukuba-shi, Ibaraki-ken 305-8566 JAPAN. The plants subjected to administration of the plant disease control agent include those in the state of seedlings. The types of plants subjected to the administration of the plant disease control agent include those belonging to the family Ericaceae, for example Rhododendron.

Further, the present invention relates to a method for producing a disease-resistant plant, characterized by inoculating Streptomyces spp. [for example, Streptomyces sp. R-5(FERM BP-7179)] into a plant. Here plants subjected to administration of the plant disease control agent include those in the state of seedlings. Types of plants subjected to the administration of the plant disease control agent include those belonging to the family Ericaceae, for example rhododendron and mountain laurel.

Furthermore, the present invention relates to a phytoalexin inducer agent comprising Streptomyces spp. [for example, Streptomyces sp. R-5(FERM BP-7179)] as an active ingredient.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

Figure 1:
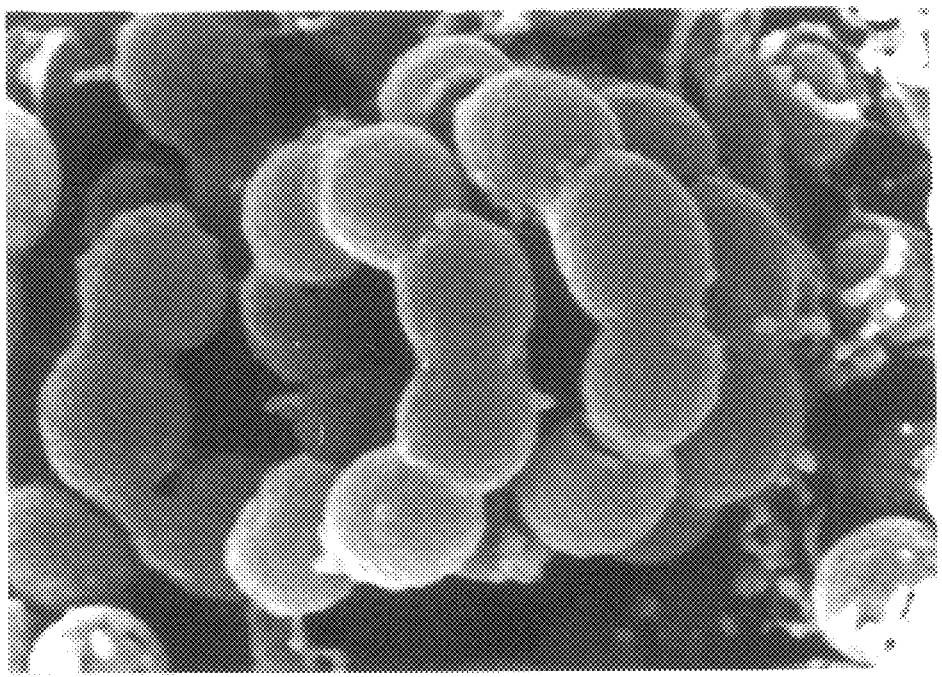
FIG. 1 is a scanning electron microscopic photograph showing spores of the R-5 strain.

The present invention will be described in detail as follows.

EXAMPLES

Unlike conventional plant disease control agents comprising a chemical substance as an active ingredient, the plant disease control agent according to the present invention relates to the plant disease control agent comprising R-5 strain of actinomycete as an active ingredient. This actinomycete, an active ingredient of the plant disease control agent of this invention can be isolated as follows.

1. Isolation of actinomycetes from a plant

Sources of R-5 strain of actinomycete include plants belonging to rhododendron and Mountain laurel grown outdoor, members of the family Ericaceae. For example, the R-5 strain of Streptomyces can be isolated from a plant as follows. A portion of the tissue (e.g., a leaf, a stem, or a root) of rhododendron grown outdoor in soil is washed with tap water. Then the sample is dipped in such as sodium hypochlorite for sterilization. The sample is then rinsed sufficiently with sterile water, and then dipped in such as ethanol solution (e.g., 70% ethanol) for re-sterilization. After drying sufficiently, the plant sample section is placed on a plate medium for isolating actinomycete and cultured under appropriate conditions. The media for isolating actinomycete include IMA-2 medium, YMA medium, YMPG medium, Bennett's-maltose medium, and glucose asparagine agar medium. If necessary, antibiotics may be added to these media.

Subsequently, colonies extending from the plant specimen on the medium are transferred onto fresh agar medium and cultured in order to isolate pure actinomycete. The isolated actinomycetes can be suspended in sterilized glycerol solution (e.g., 20% glycerol) for cryopreservation. In the present invention, 17 strains of actinomycetes, named R-1 to R-17 strains, respectively, were isolated. One of these 17 strains is R-5 strain.

2. Examination of antimicrobial activity of isolated actinomycetes

The antimicrobial activity of actinomycetes can be examined using the dual culture method as follows. The dual culture method examines how a subject actinomycete influences the growth of indicator organisms by inoculating and culturing indicator organisms (hereinafter referred to as indicator organisms for antimicrobial activity) which indicate the presence or absence and the strength of antimicrobial activity of the actinomycete, on the same plate medium. For example, indicator organisms for antimicrobial activity and actinomycetes isolated as described in 1 are inoculated and cultured on the same plate medium while leaving an appropriate distance between them, such as 4 to 5 cm. Another plate medium is prepared as a control, on which only indicator organisms for antibiotic activity is inoculated. After culturing, the growth of indicator organisms for antimicrobial activity in the dual culture medium and that in the control plate medium are compared. The growth inhibition zone width of the indicator organisms for antimicrobial activity is evaluated according to the following table. The indicator organisms for antimicrobial activity include, but are not limited to, fungi belonging to the genus Phytophthora or the genus Pestalotiopsis. Among R-1 to R-17 strains of actinomycetes isolated in the above 1 according to the present invention, the R-5 strain has the widest antibiotic activity against microorganisms including the genus Phytophthora and the genus Pestalotiopsis.

TABLE 1

| Antibiotic activity evaluation | |
|---|---|
| Antibiotic activity | Growth inhibition zone width X |
| +++ | X > 20 mm |
| ++ | 20 mm ≧ X > 10 mm |
| + | 10 mm ≧ X > 1 mm |
| ± | 1 mm ≧ X |
| − | X = 0 |

3. Taxonomical determination of actinomycetes

The isolated actinomycetes can be taxonomically identified by their morphological characteristics, culture properties, physiological properties, and the like. The R-5 strain isolated according to the present invention has been identified as an actinomycete belonging to Streptomyces. The R-5 strain was deposited as FERM P-17764 with the National Institute of Bioscience and Human-Technology, Agency of Industrial Science and Technology (1-3, Higashi 1-chome, Tsukuba-shi, Ibaraki-ken 305-0046, Japan), on Mar. 1, 2000. This deposition was then transferred as FERM BP-7179 to International Deposition under the Budapest Treaty on Jun. 2, 1999.

4. Production of Disease-resistant Plant

A disease-resistant plant can be produced by inoculating the R-5 of Streptomyces sp., which is isolated according to the present invention and has growth inhibition activity against plant pathogens, into a plant.

(1) Preparation of cell suspension of Streptomyces sp. R-5

The cell suspension of Streptomyces sp. R-5 can be prepared as follows. The R-5 of Streptomyces sp. isolated in 1 above is grown in a liquid or solid medium. When the R-5 strain is grown in a liquid medium, cells are recovered by centrifuging the culture broth and the cells are suspended in an appropriate buffer to achieve a desired concentration, thereby preparing the cell suspension. When the R-5 strain is grown on a solid medium, buffer is added to the culture product, colonies grown on the surface of the solid medium are suspended sufficiently, and then the cells are recovered by centrifugation. Next the recovered cells are suspended in an appropriate buffer so as to achieve a desired concentration, thereby preparing the cell suspension.

(2) Raising of plants to be inoculated with Streptomyces sp. R-5

Plants to be inoculated with the R-5 of Streptomyces sp. can be raised by techniques generally employed in the field of floriculture. Here the plants subjected to this inoculation include not only dicotyledonous and monocotyledonous plants, but also various plants. These plants include ornamental plants for floriculture, such as those belonging to the family Ericaceae (for example rhododendron and mountain laurel), Theaceae and Rosaceae. They can be raised in a plastic green house under artificial light or outdoor under natural light. Preferably plants are raised aseptically because the plants are inoculated with an actinomycete according to the present invention.

When rhododendron is raised, first, flower buds of rhododendron are collected and dipped in ethanol or sodium hypochlorite or the like to sterilize the surface. Next florets are cut from these buds in a clean bench, and then planted on media for collecting buds. Pedicels are cultured aseptically in a culture compartment at 20° C. to 25° C. under artificial light (about 4,000 to 5,000 luxes, 12 to 14 hours/day) for 1 to 2 months, thereby allowing the pedicels to form calli. Aseptical culture is further continued for 1 to 2 months so that seedlings having stems and leaves are formed, raising plants to be inoculated with the actinomycete. Next, the seedlings are taken out of their container in the clean bench and they are separated aseptically into individual plants. Each seedling is planted in a fresh multiplication medium for ornamental plants, and cultured aseptically in a culture compartment at 20° C. to 25° C. under artificial light (about 4,000 to 5,000 luxes, 12 to 14 hours/day), thereby obtaining plants to be inoculated with the actinomycete.

(3) Inoculation of actinomycete into plants

The R-5 of Streptomyces sp. can be inoculated to the seedlings as follows. For example, the cell suspension of R-5 as prepared in the above (1) is applied over the surface of a multiplication medium on which plants (e.g., seedlings) are aseptically raised. The applied R-5 invades and infects the plants on the medium, gradually enlarging its habitat from the lower to the higher part of the plants. That is, the plant surface is covered by R-5 mycelia, thus the plants express resistance against foreign enemies, such as plant pathogens. Other than the above method for inoculating actinomycete, actinomycete can be directly inoculated into a plant by applying or spraying the cell suspension onto plants.

(4) Raising of plants inoculated with R-5 of Streptomyces sp.

Plants inoculated with the R-5 of Streptomyces sp. can be raised as follows. Plants inoculated with the actinomycete in (3) above are taken out of their container in a clean bench and separated aseptically into individual plants. Each of them is planted on a rooting medium for tissue-cultured seedlings of ornamental plants in an incubator. Seedlings are raised and cultured in a culture compartment at 20° C. to 25° C. under irradiation (about 4,000 to 5,000 luxes, 12 to 14 hours/day) for 30 days to 40 days.

After the plants are taken out of the incubator, they are separated into individual plants in water to prevent from drying. Individual plants are put into containers by size. Subsequently, each of them is dipped in indole butyric acid solution for several hours to promote its rooting. Then young plants are planted one by one using tweezers so that they are inserted into a cell tray containing soil for raising seedlings. The soil for raising seedlings used herein may be the one wherein appropriate amounts of peat moss (Izumi Nozai Co., Ltd.), perlite (Mitsui Mining & Smelting Col., Ltd.), vermiculite (manufactured by Nitto Hiruishi Co.), SaturAid (surfactant) (manufactured by Ocean Trading Co.), and FFC2000 (soil-improving activity agent) (manufactured by FFC Japan Co.) are mixed.

Next, the cell trays into which seedlings are transplanted are put into sealed vinyl tunnels. Water is supplied by automatic misting. For example, rhododendron roots within about 2 weeks. After 1 month, seedlings are acclimatized to open air with low humidity by gradually removing the vinyl tunnels. Acclimation is completed in 2 months. The plants are transferred to a facility where the plants can get sufficient sunshine and aeration, allowing the seedlings to grow. Liquid fertilizer is applied at intervals of 10 to 15 days. After about 6 months, the plants can be shipped as cell-formed seedlings having resistance against plant diseases.

5. Plant disease control agent and phytoalexin inducer agent according to the present invention The R-5 strain isolated according to the present invention can be employed as an active ingredient of a plant disease control agent because it shows no pathogenicity to plants but can give plant disease resistance to plants. Further, the R-5 strain can be employed as an active ingredient of a phytoalexin inducer agent because it can promote synthesis of a red pigment, which is an anthocyan pigment having antibiotic activity, in plant bodies.

The R-5 strain used in the production of the plant disease control agent and phytoalexin inducer agent can be those grown by well known culture methods, such as the solid, liquid or material (e.g., bran) culture method. Culture types and conditions are not limited so far as live cells can be obtained.

The plant disease control agent and the phytoalexin inducer agent, including the R-5 strain as an active ingredient, can be produced by simply suspending spores of the R-5 strain or cultured cells in a liquid, such as water. Further, the plant disease control agent and the phytoalexin inducer agent can also be produced as liquid, powdery, and granular products by mixing other ingredients. These other ingredients include a liquid carrier, a solid carrier, surfactant, such as an emulsifier, dispensing agent, and antifoamer, and an adjuvant. Specifically the liquid carriers include phosphoric acid buffer, carbonic acid buffer, and physiological saline. The solid carriers include natural mineral powders, such as kaolin, clay, talc, chalk, chalcedony, attapulgite, montmorillonite, and diatomite; synthesized mineral powder, such as silicic acid, alumina, and silicate; and polymeric natural products, such as crystalline cellulose, cornstarch, gelatine, and alginic acid. One or a mixture of two or more of these carriers can be used. The surfactants include polyoxyethylene-fatty acid ester, polyoxyethylene-fatty alcohol ether, alkylaryl polyglycol ether, alkylsulfonate, alkylsulfate, and arylsulfonate. The adjuvants include carboxymethyl cellulose, polyoxyethyleneglycol, gum Arabic, starch, and lactose.

When the plant disease control agent and the phytoalexin inducer agent according to the present invention are produced as a liquid product containing aqueous solvent as a carrier, water-soluble polymer can be added to improve the hydration of the R-5 cells in the solvent. The water-soluble polymers include polyvinyl alcohol, polyethylene glycol, polyvinyl methyl ether, polyvinyl amine, polyvinyl pyrrolidone, polyethylene imine, and polyacrylamide. To improve the stability of the R-5 strain in products by increasing the adhesive property of the R-5 strain to plants, polysaccharides, such as xyloglucan and guar gum can be mixed with the products.

The R-5 strain content contained in the plant disease control agent and the phytoalexine inducer agent according to the present invention is 0.01 to 10 weight % for a liquid product, 0.01 to 50 weight % for a granular product and 0.01 to 50 weight % for a powder product. These concentrations may be changed if necessary. Granular and powdery products may be diluted for use at 1:100 to 1:5,000, or preferably at 1:500 to 1:1,000 of the product weight with water.

The plant disease control agent and the phytoalexine inducer agent according to the present invention may be administered directly to plants by such as spraying, misting, dusting, sprinkling, injecting, or applying. Further the plant disease control agent and the phytoalexine inducer agent according to the present invention may also be administered to media or soil on which target plants grow.

A dose of the plant disease control agent or the phytoalexine inducer agent according to the present invention differs depending on administration method for them. For example in a spraying method, preferably an active ingredient of 0.1 g to 10 g per rhododendron plant is sprayed.

Plant pathogenic microorganisms to be administered with the plant disease control agent according to the present invention include fungi belonging to the genus Pestalotiopsis and the genus Phytophthora. Specifically, fungi belonging to the genus Pestalotiopsis include *Pestalotiopsis sydowiana, Pestalotiopsis longiseta, Pestalotiopsis populinigrae*, which cause leaf blight to the leaves of trees and a variety of ornamental plants, such as the family Ericaceae, the family Theaceae, and the family Rosaceae. Here the term "leaf blight" refers to a damage due to a disease that causes brown spots on the leaves or the leaves to be speckled with necrosed spots, or can result in defoliation if it is serious. This damage is a disease that injures the leaves so that it damages the commercial value of ornamental plants.

Fungi belonging to the genus Phytophthora include *Phytophthora infestans, Phytophthora cinnamomi, Phytophthora capsici, Phytophthora megasperma, Phytophthora nicotianae*, and *Phytophthora parasitica*, which cause blight to the roots, the near-ground part of stems, and the leaves of a variety of plants, such as the family Solanaceae, the family Ericaceae, the family Liliaceae, the family Cucurbitaceae, and the family Poaceae. Here the term "blight" is referred to as an infectious disease having strong epidemic potential that rapidly softens and rots plant tissues, thereby causing the whole plant to be killed.

EXAMPLES

The present invention will now be described in detail by way of examples, but is not limited thereto.

Example 1

Isolation of Actinomycete Having Antimicrobial Activity (1) Isolation of actinomycetes from plants Actinomycetes were isolated from the leaves, stems or roots of potted rhododendron seedlings (variety Sakigake) as follows. Specimens of about 1×2 mm² collected from the leaves, stems or roots of potted rhododendron (variety Sakigake) were washed well with running tap water. After these specimens were dipped in 0.1% Tween 20 for a few seconds, dipped in 1% sodium hypochlorite for 5 minutes, then washed with sterile distilled water for a few minutes. Subsequently, the specimens were dipped in 70% ethanol for 1 minute, and then the surfaces were dried sufficiently in a clean bench.

Thus the plant specimen whose surface was thus sterilized was placed on a plate medium (IMA-2) supplemented with antibiotics in a Petri dish for isolating actinomycetes, and then cultured in an incubator at 30° C. for 1 month. The compositions for the IMA-2 medium and the added antibiotic solution are as shown in Tables 2 and 3, respectively. Each ingredient of IMA-2 medium was dissolved in distilled water, and then sterilized by an autoclave at 120° C. for 20 minutes. Ten ml of antibiotic solution was added to 1,000 ml of IMA-2 medium.

TABLE 2

| IMA-2 Medium Composition | |
|---|---|
| Ingredient | Amount added |
| Glucose | 50 g |
| Soluble starch | 5.0 g |
| Meat extract | 1.0 g |
| NZ-casein | 2.0 g |
| Salt | 2.0 g |
| Calcium carbonate | 1.0 g |
| Powdery agar | 15.0 g |
| Distilled water | 1,000 ml |

TABLE 3

| Antibiotic solution composition | |
|---|---|
| Ingredient | Amount added |
| Amphotericin B (WAKO Pure Chemical Industries Ltd.,) | 50 mg |
| Rifampin-viccilin solution [rifampin (Calbiochem Co.) 0.02 g; Viccilin (Meiji Seika Kaisha Ltd)] 1 g; 100% ethanol 16 ml; distilled water 4 ml] | 10 ml |
| 30-fold Heritage (Zeneca) | 10 ml |
| Distilled water | 1,000 ml |

Mycelia of actinomycete extending from the surface of the plant specimen placed on IMA-2 medium were collected using one end of a sterilized thin glass tube, transferred onto a freshly prepared IMA-2 plate medium, then cultured at 30° C. for a few days. Each of colonies grown on the medium was inoculated onto a membrane filter (Mixed cellulose ester, f 0.2 mm, Advantec) on another IMA-2 medium, and cultured at 30° C. for a week. After the membrane filter was removed, colonies grown on the medium surfaces were separated by their shapes. Each colony was suspended in 20% glycerol and stored in a freezer at −80° C. until use. A total of 17 strains were obtained. These 17 strains were named R-1 to R-17, respectively.

(2) Selection of strains capable of growing on multiplication medium for seedlings of ornamental plants The stored 17 strains were transferred onto a freshly prepared IMA-2 plate medium and cultured at 30° C. for a few days. Subsequently, each strain was inoculated on a multiplication medium for seedlings of ornamental plants, then cultured at 25° C., and growth of the strains was examined. The composition of the multiplication medium for the seedlings of ornamental plants (herein after referred to as a multiplication medium for ornamental plants) is as shown in Table 4.

TABLE 4

Multiplication medium ornamental plants

| Ingredient | Amount added |
|---|---|
| $NH_4CO_3$ | 400 mg |
| $KNO_3$ | 480 mg |
| $MgSO_4.7H_2O$ | 370 mg |
| $FeSO_4.7H_2O$ | 55.7 mg |
| $Na_2.EDTA$ | 74.5 mg |
| $CaCl_2 2H_2O$ | 440 mg |
| $MnSO_4 H_2O$ | 16.9 mg |
| $ZnSO_4.7H_2O$ | 8.6 mg |
| $H_3BO_3$ | 6.2 mg |
| KI | 0.83 mg |
| $CoCl_2.6H_2O$ | 0.025 mg |
| $CuSO_4.5H_2O$ | 0.025 mg |
| $Na_2MoO_4.2H_2O$ | 0.25 mg |
| $NaH_2PO_4 H_2O$ | 380 mg |
| myo-inositol | 100 mg |
| Adenine sulfate.$2H_2O$ | 80 mg |
| Thiamin hydrochloride | 0.4 mg |
| $N^6$(2-isopentenyl)-adenine | 5.0 mg |
| Sucrose | 30 mg |
| Pairogen (Akatsuka Co. Ltd.) | 0.3 ml |
| Powdery agar | 8.0 g |
| Distilled water | After the above ingredients were dissolved, a total of 1,000 ml of medium was prepared. pH was adjusted to 4.5 using 1N NaOH |

Table 5 shows the results of growth of R-1 to R-17 strains. As shown in Table 5, 10 strains, R-1, 4, 5, 6, 8, 9, 10, 11, 13 and 14, could grow on a multiplication medium for seedlings among the 17 strains of actinomycetes.

TABLE 5

Growth of actinomycetes strains on multiplication medium for seedlings of ornamental plants

| Degree of growth | Actinomycetes strains |
|---|---|
| ++ | R-5, R-13 |
| + | R-1, R-4, R-6, R-8 R-9, R-10, R-11, R-14, |
| - | R-2, R-3, R-7, R-12, R-15, R-16, R-17 |

(Degree of growth)
++: extremely good growth,
+: good growth,
-: no growth (3) Determination of antimicrobial activity of isolated actinomycetes against plant pathogens The antimicrobial activities of 10 strains of actinomycetes selected in (2) above against plant pathogens, Phytophthora and Pestalotiopsis fungi, were determined by dual culture using these fungi. The above Streptomyces and the plant pathogens, *Phytophthora cinnamomi* MAFF No. 305565 and *Pestalotiopsis sydowiana* MAFF No. 305755, were inoculated on IMA-2 plate medium in a Petri dish, leaving a distance of about 5 cm from each other, and cultured at 28° C. Subsequently, the growth inhibition zone width formed between the colony of actinomycete and that of the plant pathogens was measured so as to determine the antimicrobial activity of the actinomycete against the plant pathogens. A control IMA-2 plate medium containing only the plant pathogens inoculated was prepared. Table 6 shows the results. As clearly shown in Table 6, the R-5 strain possessed the highest antimicrobial activity against the two plant pathogens, Phytophthora and Pestalotiopsis fungi.

TABLE 6

Antimicrobial activity of actinomycete strains

| actinomycete strains | Antimicrobial activity against indicator *fungi* | |
|---|---|---|
| | *Phyntophthora cinnamomi* | *Pestalotiopsis sydowiana* |
| R-1 | + | +++ |
| R-4 | ± | ++ |
| R-5 | +++ | +++ |
| R-6 | ± | ± |
| R-8 | - | ± |
| R-9 | + | +++ |
| R-10 | - | ± |
| R-11 | ++ | ++ |
| R-13 | - | ± |
| R-14 | + | ++ |

(Antibiotic activity)
+'+: inhibition zone width (X) >20 mm,
++: 20 mm ≧ X > 10 mm,
+: 10 mm ≧ X > 1 mm,
±: 1 mm ≧ X,
-: X = 0

Example 2

Taxonomic Identification of Isolated Actinomycete (1) Morphological characteristics of R-5 strain The morphological characteristics of the R-5 strain obtained in Example 1 were observed using a scanning electron microscope. First the R-5 strain cultured at 30° C. for 7 days on IMA-2 plate medium was hollowed out together with the agar medium and then pasted to a sample stage. Then the R-5 strain together with the stage was frozen by dipping in liquid nitrogen. Next, the sample was inserted into a cryosystem of a scanning electron microscope, covered with a ultrathin gold film, then observed using a scanning electron microscope (S4000, manufactured by Hitachi Ltd.). FIG. 1 shows the image of mycelia of the R-5 strain observed. As shown in FIG. 1, the R-5 strain possesses 10 to 50 spores forming a line and making a spiral shape as a whole. Each spores is 0.4 to 0.6×0.3 to 0.4 μm in size, elliptical in shape, and has a smooth surface.

(2) Properties of R-5 strain on various media

The properties on media and physiological properties of the R-5 strain were examined according to Shirling, E. B. and colleagues' method (International Journal of Systematic Bacteriology 16(3): 313–340 (1996)) which is recommended by International Sterptomyces Project (ISP) and Experimental Method for Identifying actinomycete (ed. The Society for actinomycetes Japan, 1972). The R-5 strains were grown on ISP-2 medium (yeast extract•malt agar medium), ISP-3 medium (oat meal agar medium), ISP-4 medium (starch•inorganic salt agar medium) and ISP-5 medium (glycerin•asparagine agar medium). Then the properties of substrate mycelia, the substrate mycelia observed from the underside of the Petri dish, aerial mycelia, and diffusive pigments; and physiological properties, such as ability to hydrolyze starch and melanin synthesis were examined. The properties on these media and the physiological properties were shown in Tables 7 and 8, respectively. The number in the parenthesis indicates the color tone number based on New Manual of Color Names, $4^{th}$ ed. (ed. JAPAN COLOR RESEARCH INSTITUTE, JAPAN COLOR ENTERPRISE CO., LTD. 1988). As shown in Table 7, the R-5 strain grew well on any media. The substrate mycelium was yellow. Mature powdery colonies exhibited gray to dark brown and formed yellow pigments.

TABLE 7

Culture properties of R-5 strain on various media

| Media | Sites observed | Culture properties |
|---|---|---|
| Yeast extract · Malt agar medium (ISP-2 medium) | Substrate mycelia | Good growth, gold (162) |
| | Inside of substrate mycelia | Bright yellow (140) |
| | Aerial mycelia | Powdery, vivid reddish yellow (110) |
| | Diffusive pigment | Light yellow (134) |
| Oat meal agar medium (ISP-3 medium) | Substrate mycelia | Pale yellow (127) |
| | Inside of substrate mycelia | Olive gray (410) |
| | Aerial mycelia | Powdery, poor formation of aerial hyphae Grayish brown (119) |
| | Diffusive pigment | None formed |
| Starch · inorgaic salt agar medium (ISP-4 medium) | Substrate mycelia | Good growth, gold (162) |
| | Inside of substrate mycelia | Gold (162) |
| | Aerial mycelia | Powdery, Good formation of aerial hyphae, reddish black (427) |
| | Diffusive pigment | Light greenish yellow (135) |
| Glycerin · asparagine agar medium (ISP-medium) | Substrate mycelia | Good growth, light yellow (134) |
| | Inside of substrate mycelia | Light greenish yellow (135) |
| | Aerial mycelia | Powdery, grayish pink (33) |
| | Diffusive pigment | Light yellow (133) |

TABLE 8

Physiological properties of R-5 strain

| Test items | Results |
|---|---|
| Ability to hydrolze starch (ISP-4 medium) | Positive |
| Melanin synthesis (tyrosine agar medium ISP-7 medium) | Negative |
| Coagulation of milk (10% skimmed milk) | Negative |
| Peptonization of milk (10% skimmed milk) | Positive |
| Possible temperature range for growth (yeast extract · starch agar medium) | 11 to 42° C. |
| Optimum temperature range for growth (yeast extract · starch agar medium) | 17 to 38° C. |
| Possible pH range for growth (Trypticase Soy broth, BBL) | pH 4 to 8 |
| Optimum pH range (Trypticase Soy Broth, BBL) | pH 5 to 6 |
| Color changes in soluble pigments by pH (Starch · inorganic salt agar medium, ISP-4 medium) | |
| 1N HCL | None changed (yellow) |
| 1N NaOH | Changed to white |
| Ability to use carbon sources (Pridham and Gottlieb agar medium) | |
| D-glucose | Positive |
| L-arabinose | Positive |
| Sucrose | Negative |
| D-xylose | Positive |
| Inositol | Negative |
| D-mannose | Positive |
| D-fructose | Positive |
| L-rhamnose | Negative |
| Raffinose | Negative |
| Cellobiose | Positive |

(3) Chemical taxonomic features of cellular constituents of R-5 strain

Acid hydrolysate was analyzed for the whole cells by the thin-layer chromatography method as described in *Experimental Method for Identifying actinomycete* (ed. The Society for Actinomycetes Japan, 1985: 62–70), and *Applied Microbiology* (Stanech J. I., et al.: in 1974, 28:226–231). As a result, the presence of LL type diaminopimelate, glycine, and galactose was confirmed. Therefore, the R-5 strain was identified as an actinomycete belonging to the genus Streptomyces based on the above morphological and chemical taxonomic properties.

Example 3

Treatment of Tissue-cultured Rhododendron Seedlings With Actinomycete and Electron Microscopic Observation of Tissue-cultured Seedlings Treated With Actinomcyete (1) Preparation of cell suspension of R-5 strain The R-5 strain was inoculated into IMA-2 liquid medium and subjected to shaking culture at 30° C. for 12 hours. Cells were recovered from the resulting culture product. Then the cell suspension of the R-5 strain was prepared at a cell density of 3 to $4 \times 10^6$ cfu/ml using 0.01M phosphoric acid buffer (pH 7.0).

(2) Formation of young plants from rhododendron organs

Flower buds of rhododendron were collected, dipped in 70% ethanol for 30 seconds, then dipped in 2% sodium hypochlorite for 10 minutes to achieve surface sterilization. In a clean bench, florets were cut from these buds and planted on initiation and establishment medium of ornamental plants shown in Table 9. These florets were cultured aseptically in a culture compartment at 25° C. under irradiation (about 4,000 luxes, 10 hours/day) for 1 to 2 months, thereby allowing pedicels to form calli. Further the culture was continued for 1 to 2 months so that seedlings having stems and leaves grew.

TABLE 9

Initiation and establishment medium of ornamental plants

| Ingredient | Amount added |
|---|---|
| $NH_4CO_3$ | 400 mg |
| $KNO_3$ | 480 mg |
| $MgSO_4.7H_2O$ | 370 mg |
| $FeSO_4.7H_2O$ | 55.7 mg |
| $Na_2.EDTA$ | 74.5 mg |
| $CaCl_2.2H_2O$ | 440 mg |
| $MnSO_4.H_2O$ | 16.9 mg |
| $ZnSO_4.7H_2O$ | 8.6 mg |
| $H_3BO_3$ | 6.2 mg |
| KI | 0.83 mg |
| $CoCl_2.6H_2O$ | 0.025 mg |
| $CuSO_4.5H_2O$ | 0.025 mg |
| $Na_2MoO_4.2H_2O$ | 0.25 mg |
| $NaH_2PO_4.H_2O$ | 380 mg |
| myo-inositol | 100 mg |
| Adenine sulfate.$2H_2O$ | 80 mg |
| Thiamin hydrochloride | 0.4 mg |
| $N^6$(2-isopentenyl)-adenine | 15.0 mg |
| Sucrose | 30 mg |
| Powdery agar | 8.0 g |
| Distilled water | After the above ingredients were dissolved, a total of 1,000 ml of medium was prepared. pH was adjusted to 4.5 using 1N NaOH |

(3) Transplantation of seedlings to multiplication medium for seedlings of ornamental plants Young plants obtained from (2) above were taken out of the container in a clean bench. The young plants were aseptically separated into individual plants, and each was planted on a freshly prepared multiplication medium for seedlings of ornamental plants shown in Table 4. The young plants were cultured aseptically in a culture compartment at 25° C. under irradiation (about 4,000 luxes, 10 hours/day).

(4) Treatment of rhododendron with R-5 strain

One ml of the R-5 strain cell suspension obtained in the above (1) was aseptically dropped onto the surface of a multiplication medium for seedlings of ornamental plants, on which rhododendron seedlings grew as in (3) above, in a clean bench. Then the dropped cell suspension was spread over the whole medium surface so that the stem base portion of rhododendron seedlings came into contact with cells of the R-5 strain. Subsequently, these seedlings were grown in an incubator at 25° C. for 1 week.

(5) Observation by a scanning electron microscopy

Rhododendron seedlings treated with the R-5 strain were observed with a scanning electron microscope as follows. Rhododendron seedlings treated with the R-5 strain and raised for a week in an incubator as described in (4) above were taken out of the container, and then cut and divided into stems and leaves. These samples were dipped in 5% glutaraldehyde containing 0.2% tannic acid, fixed at room temperature for 6 hours, and then dipped in 5% glutaraldehyde containing 2% tannic acid for 6 hours. After washing thoroughly with water, these samples were fixed with 1% osmium tetraoxide for 12 hours. After washing thoroughly with water, the specimens were dehydrated by dipping in 30, 50, 70, 90, 95, and 100% ethanol in order. Ethanol 100% was replaced with isoamyl acetate. The specimens were dried by a critical point dryer, onto which gold was deposited, and then observed with a scanning electron microscope.

Figure 2:
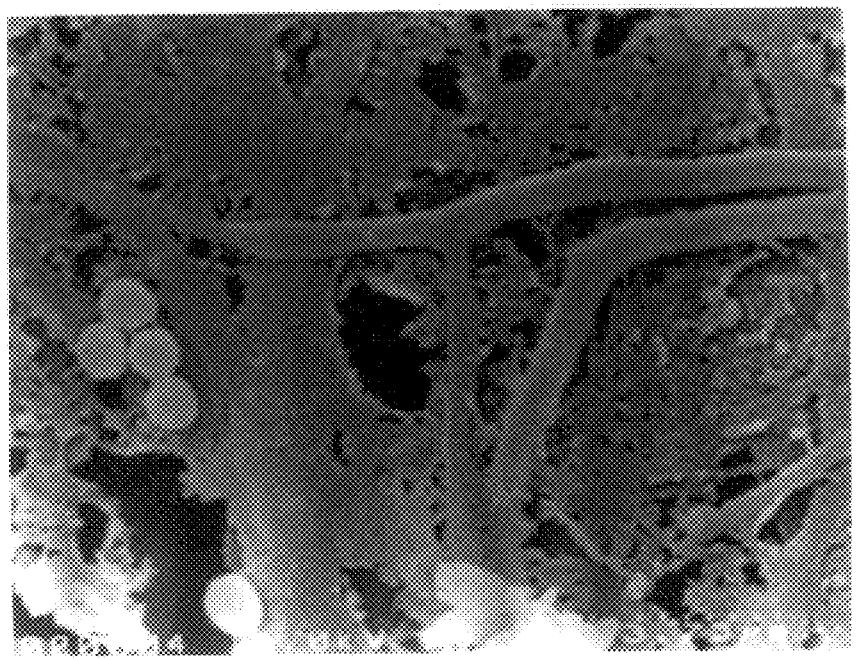
FIG. 2 is a scanning electron microscopic photograph showing how the R-5 strain grew on the stem surface.
Figure 3:
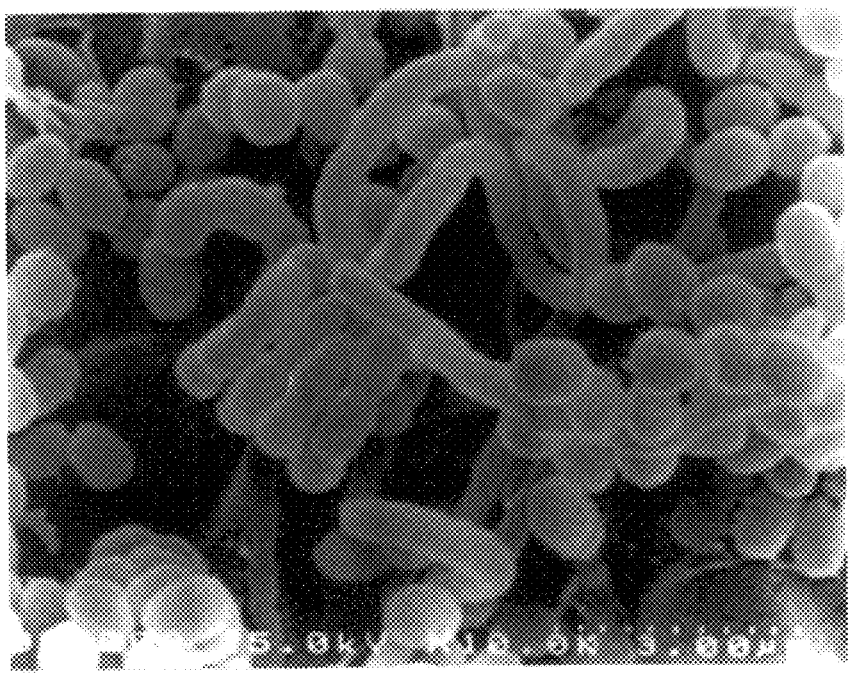
FIG. 3 is a scanning electron microscopic photograph showing how R-5 strain grew on the stem surface. Note the spore chains.

FIGS. 2 and 3 are scanning electron micrographs showing the R-5 strain growing on the stem surface. As shown in FIG. 2, mycelia extended on a wax layer on the stem surface, and grew everywhere under the wax layer. As shown in FIG. 3, mycelia of the R-5 strain growing on the stem surface formed a spore chain. That is, spores formed chain-like strings, and were spiral as a whole. Each spore possessed 0.4 to 0.6×0.3 to 0.4 µm in size, globular or oval shape, smooth surface. That is, appearance of the spore chain and spores was same as that on IMA-2 medium observed in Example 2 (1). Similar observation made for the leaves resulted in similar results. Therefore, it was shown that inoculation of the R-5 strain on the surface of multiplication media for ornamental plants, on which rhododendron seedlings were raised, allows the R-5 strain to grow mycelia and form spores on the surfaces of stems and leaves within a week.

(6) Observation using a fluorescence microscope

Rhododendron seedlings of the R-5 strain were observed using a fluorescence microscope as follows. Rhododendron seedlings treated with the R-5 strain and raised in an incubator for a week in (3) above were taken out of the container. Pieces of about 1×2 mm² each were prepared from the leaves. After dipping in 0. 1% Tween 20 for a few seconds, these sections were dipped in 1% sodium hypochlorite for 5 minutes, followed by thorough washing with sterile distilled water for a few minutes. Subsequently the pieces were dipped in 70% ethanol for 1 minute, and then the surfaces were dried sufficiently in a clean bench. Thus surface-sterilized pieces were placed on IMA-2 plate medium supplemented with antibiotics in a Petri dish, and cultured in an incubator at 30° C. for about a week. The leaf pieces were dipped in 3% formaldehyde (pH 7.4) containing Triton X 100 in a glass bottle. Formaldehyde was infiltrated into the pieces under reduced pressure for 3 hours. After washing thoroughly with water, the samples were fixed with 1% osmium tetraoxide for 12 hours. After washing thoroughly with water, the samples were dehydrated by dipping in 30, 50, 70, 90, 95, and 100% ethanol in order for 20 minutes each. Subsequently the samples were embedded in historesin, filled with nitrogen gas, and then solidified in a refrigerator at 4° C. overnight. A ultrathin section 0.7 µm in width was cut using a microtome equipped with a glass knife. The section was placed and fixed on a glass slide by heating the glass slide to 50 to 60° C. on an electric heating board. 0.01% acridine orange was dropped onto the sections and then a cover glass was applied on the sections, then observed using a UV irradiation fluorescence microscope.

Figure 4:
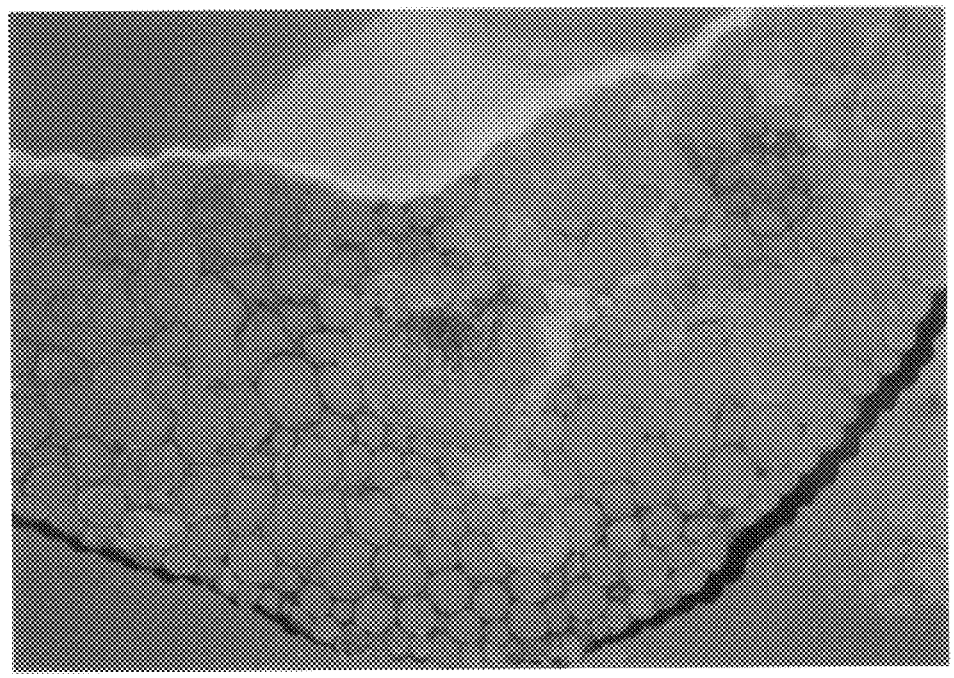
FIG. 4 is a fluorescent microscopic photograph showing how the R-5 strain grew inside the leaf. (Orange color: R-5 mycelia and spores.)

FIG. 4 is a fluorescence microscopic photograph showing the R-5 strain growing inside the leaf. The R-5 strain emits yellowish orange fluorescence. As shown in FIG. 4, the R-5 strain grew particularly in cells and intercellular spaces of mesophyll tissue, and flew outside of the leaf during culture. Therefore, it was shown that when the surface of multiplication medium for ornamental plants, on which rhododendron young plants are grown, is treated with R-5 strain, R-5 strain invades inside the leaf, particularly growing in cells and intercellular spaces of mesophyll tissue.

Example 4

Distribution of Actinomycete in Rhododendron Seedlings Treated With Actinomycete Distribution of actinomycete growing in and on rhododendron seedlings was examined by re-isolating actinomycete from each site of the plant when a certain period of time had elapsed after the treatment with the R-5 strain. First, the R-5 strain was inoculated on the surfaces of multiplication media for ornamental plants, on which rhododendron seedlings were raised in the same manner as in Example 3 (3). Then the seedlings were raised under irradiation (about 4,000 luxes, 12 hours/day) in an incubator at 25° C. for 8 days. Everyday from day 1 to day 8, some of seedlings were taken out of their container and their stems with leaves were cut at every node in a clean bench. This section was dipped in 0.1% Tween 20 for a few seconds, dipped in 1% sodium hypochlorite for 5 minutes, then washed well with sterile distilled water for a few minutes. After dipping in 70% ethanol for a minute, the surface of the sections was thoroughly dried in a clean bench. Next, each of surface-sterilized nodes was placed on IMA-2 plate medium supplemented with antibiotics in a Petri dish, and cultured in an incubator at 30° C. for about a week. By observing whether R-5 strain grew or not on the medium, the re-isolation ratio of the R-5 strain was examined. Table 10 shows the re-isolation ratio at each node of the plants. In fractions in Table 10, denominators represent the number of sample plants and numerators represent the number of plants from which the R-5 was isolated.

TABLE 10

Re-isolation ratio of R-5 strain from rhododendron seedlings treated with R-5 strain

| Days after inoculation with R-5 strain | Near-ground portion | Sites | | | | |
|---|---|---|---|---|---|---|
| | | 1st node | 2nd node | 3rd node | 4th node | 5th node or above |
| 1 | 0/3 | 0/3 | 0/3 | 0/3 | 0/3 | 0/3 |
| 2 | 2/3 | 2/3 | 0/3 | 0/3 | 0/3 | 0/3 |
| 3 | 2/3 | 1/3 | 1/3 | 0/3 | 0/3 | 0/3 |
| 4 | 2/3 | 1/3 | 1/3 | 0/3 | 0/3 | 0/3 |

TABLE 10-continued

Re-isolation ratio of R-5 strain from rhododendron seedlings treated with R-5 strain

| Days after inoculation with R-5 strain | Near-ground portion | Sites | | | | |
|---|---|---|---|---|---|---|
| | | $1^{st}$ node | $2^{nd}$ node | $3^{rd}$ node | $4^{th}$ node | $5^{th}$ node or above |
| 5 | 3/3 | 2/3 | 1/3 | 0/3 | 0/3 | 0/3 |
| 6 | 3/3 | 2/3 | 1/3 | 0/3 | 0/3 | 0/3 |
| 7 | 4/4 | 2/4 | 2/4 | 2/4 | 1/4 | 1/4 |
| 8 | 5/5 | 5/5 | 3/5 | 2/5 | 1/5 | 1/5 |

Figure 5:
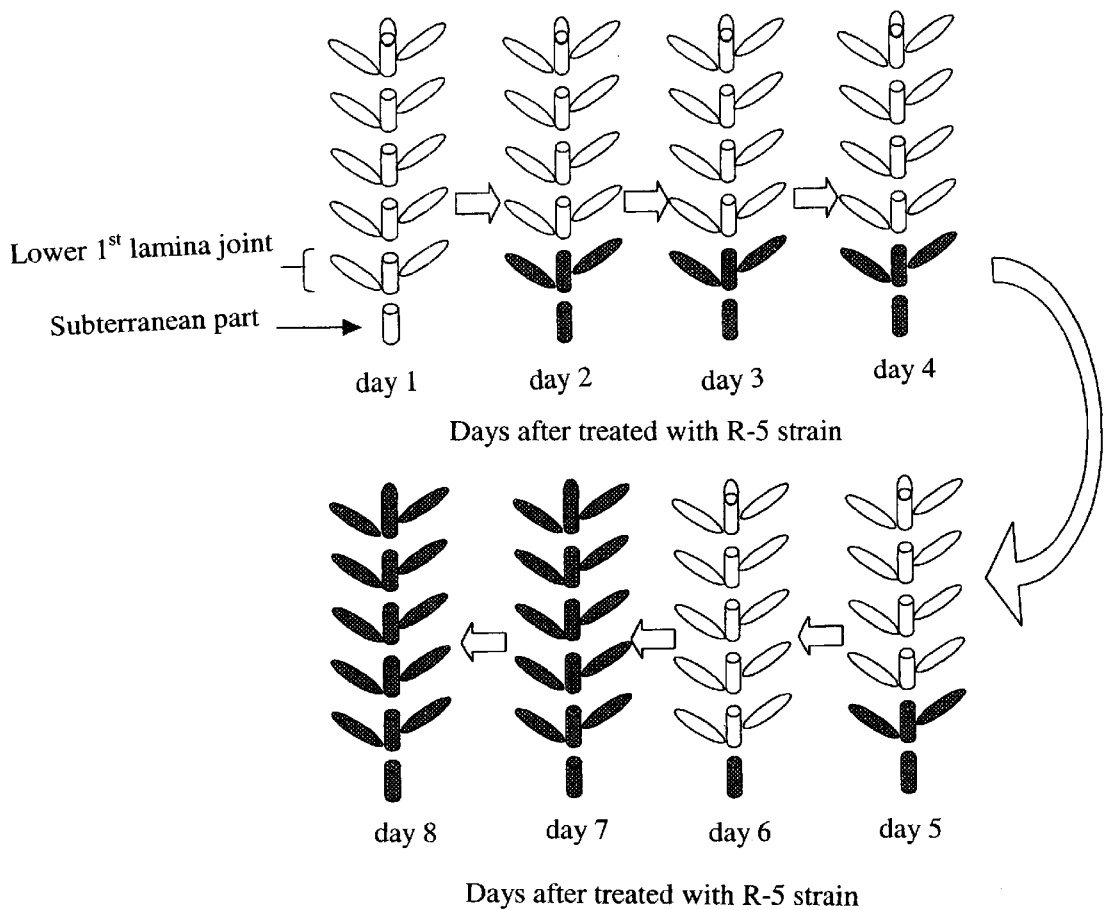
FIG. 5 shows how the R-5 strain grew on a rhododendron plant. Dark portions represent the nodes from which R-5 was re-isolated.

As shown in Table 10, the R-5 strain inoculated on the surfaces of the medium expanded to grow to the upper portions of the plants with time as in FIG. 5. On day 8 after the inoculation, inoculated actinomycete grew on the sites even at the $5^{th}$ node or above.

Example 5

Production of Rhododendron Having Resistance to Plant Pathogens (1) Preparation of a plant pathogen

*Pestalotiopsis sydowiana*, which has been stocked on a slant potato dextrose agar medium, was inoculated on a potato dextrose agar plate medium and cultured for a week in an incubator at 25° C. This plant pathogen extended its hyphae and formed white colonies. Colonies that had formed on the agar medium were cut together with agar into a disc 4 mm in diameter in a clean bench. The disc was used as an inoculum of the plant pathogen in the following experiment.

(2) Inoculation of the pathogen to rhododendron seedlings

The plant pathogen was inoculated to rhododendron seedlings that had been treated with actinomycete. Resistance of these seedlings to the plant pathogen was examined. The R-5 strain was inoculated onto the surface of a multiplication medium for ornamental plants, on which rhododendron seedlings were growing according to the procedures in Example 3 (3). Next, the seedlings were raised in an environmental control room at 25° C. under irradiation (about 4,000 luxes, 12 hours/day) for a week. After that, one of the inoculum disks as prepared in the above (1) was placed on a leaf at the upper $4^{th}$ node of the seedlings treated with the R-5 strain. As a control, one of the inoculum disks as inocula was placed also on a leaf at the upper $4^{th}$ node of the seedlings untreated with the R-5 strain. Then, both seedlings treated and untreated with the R-5 strain were raised in an incubator at 25° C. under irradiation (about 4,000 luxes, 12 hours/day) for 2 weeks.

Figure 6:
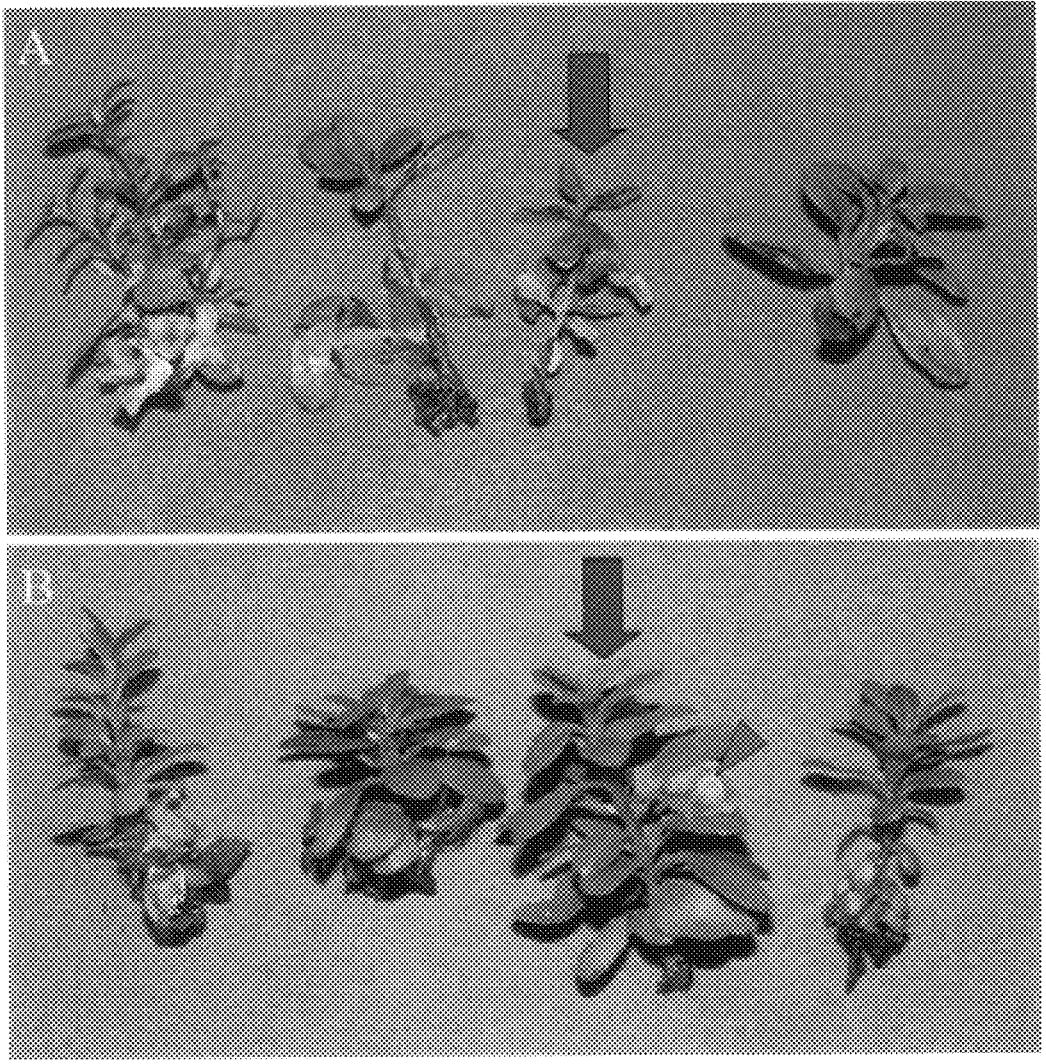
FIG. 6 are photographs showing the disease conditions of rhododendron plants untreated (A) and treated with the R-5 strain (B), respectively.

(3) Disease condition of rhododendron seedlings inoculated with the plant pathogen FIGS. 6(A) and (B) show a photograph of rhododendron seedlings untreated with R-5 strain and a photograph of those treated with R-5 strain, respectively. Comparison of the plant indicated by an arrow in A and the one in B of FIG. 6, suggests that in the rhododendron seedlings untreated with R-5 strain (as indicated by an arrow in A of FIG. 6) the leaf inoculated with the pathogen was covered by hyphae and discolored to brown. However, in the seedlings treated with R-5 strain (as indicated by an arrow in B of FIG. 6) only the leaf inoculated with the pathogen was covered by hyphae (as indicated by a triangle) and discolored brown, and hyphae did not grow beyond the inoculated leaf to the upper and lower stems and leaves.

Further rhododendron seedlings untreated (control block) and those treated with the R-5 strain (R-5 strain-treated block) were observed on day 7 and 14. The symptom indexes were evaluated with four stages (no symptom, only the inoculated leaves discolored to brown, the inoculated leaves discolored and the upper and lower leaves and part of stems discolored, and entire seedlings wilted). Table 11 shows the results.

TABLE 11

Effect of treatment with R-5 strain for rhododendron seedlings on incidence of symptom (discoloration) due to *Pestalotiopsis sydowiana*

| | | Symptom Incidence | |
|---|---|---|---|
| Treatment | Symptom | Day 7 | Day 14 |
| Control Block | No symptom | 7% | 0% |
| | Only inoculated leaves discolored | 43% | 11% |
| | Inoculated leaves, upper and lower leaves, and part of stems discolored | 50% | 36% |
| | Entire seedlings wilted | 0% | 54% |
| R-5 Strain-Treated Block | No symptom | 6% | 8% |
| | Only inoculated leaves discolored | 94% | 92% |
| | Inoculated leaves, upper and lower leaves, and part of stems discolored | 0% | 0% |
| | Entire seedlings wilted | 0% | 0% |

As shown in Table 11, entirely wilted seedlings reached 54% on day 14 on the control block, but no entirely wilted seedlings were found on the R-5 strain-treated block.

These results suggest that treating tissue-cultured rhododendron seedlings with R-5 strain can escape significantly from damages due to *Pestalotiopsis sydowiana*.

Example 6

Disease Resistance Test Against Root Rot Fungus

Culture-soil 10 g [Peat moss: Vermiculite =7:3 (v/v)] and 50 ml of ion exchange water were added to a plastic pot (6 cm×6 cm×9 cm), and subjected to autoclave sterilization (at 121° C. for 20 minutes, then 24 hours later, at 121° C. for 20 minutes) to prepare sterilized soil. On the other hand, 30 mycelial disks were prepared by stamping out the mycelial mat of the root rot filamentous fungus *Phytophthora cinnamomi* MAFF No. 305565 cultured for 10 days on potato dextrose agar medium. The 30 mycelial disks were mixed with the sterilized soil. Next, the same amount of sterilized soil was spread over the culture-soil containing the pathogenic filamentous fungus to prepare the contaminated soil. The surfaces of the multiplication medium of flowering plant, on which rhododendron seedlings were growing, were treated with the mycelial solution of R-5 strain, and cultured at 25° C. for 10 days under light at about 4,000 luxes for 12 hours/day. After culturing, rhododendron seedlings were pulled out. Five seedlings pot were planted in the contaminated soil, and the lids were put on the pots. Then, the seedlings were cultured at 25° C. under light (about 4,000 luxes for 12 hours/day) as described above. In addition, untreated seedlings were planted in the contaminated soil in the same manner as described above to prepare the control block. Two weeks later, the seedlings were observed and evaluated with the symptom index with 3 stages [no symptom (healthy), part of seedlings discolored, and seedlings wilted].

Figure 7:
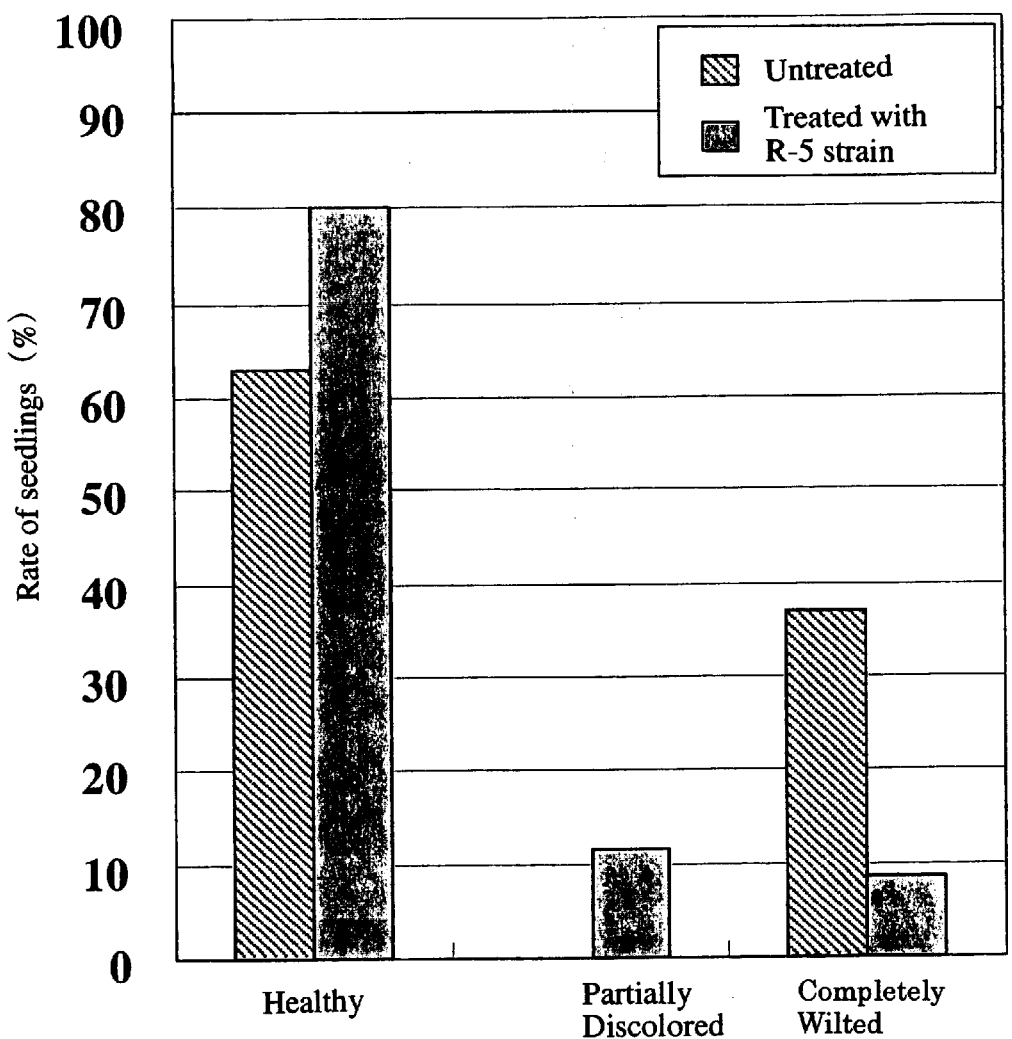
FIG. 7 is a graph showing the symptom indexes of rhododendron plants, infected with a root-rot pathogen, treated and untreated with the R-5 strain.

FIG. 7 shows the results. As shown in FIG. 7, on the untreated block, about 40% of the seedlings wilted completely two weeks after the transplantation of the culture-soil, and only about 60% of them remained healthy. However in the R-5 strain-treated block, about 80% of the seedlings remained healthy whereas about 11% of them showed partial discoloration of the stems or the leaves and about 8% of them entirely wilted. Hence, it was shown that treating tissue-cultured rhododendron seedlings with R-5 strain can significantly escape from root rot due to *Phytophthora cinnamomi*.

Example 7

Induction of Phytoalexin by Treatment with Actinomycete

Figure 8:
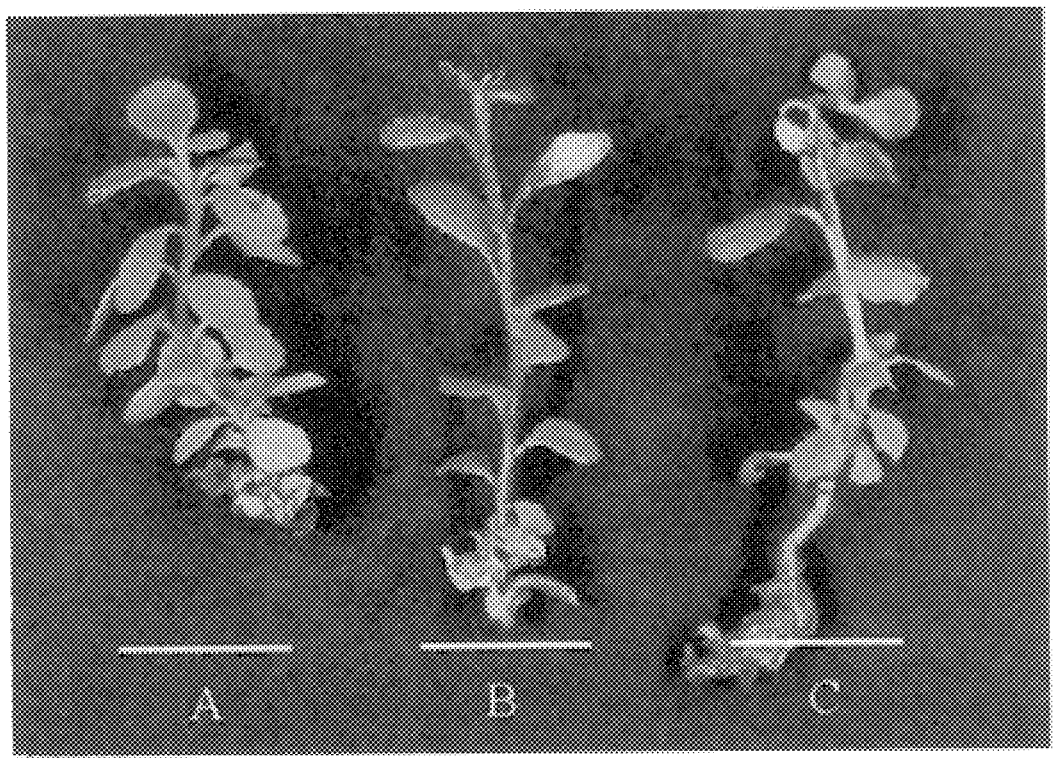
FIG. 8 is a photograph showing the color of stems of rhododendron plants treated and untreated with the R-5 strain. Note a green stem of R-5 untreated seedling (A), a red stem of R-5 treated and Pestalotiopsis-inoculated seedling (B); slightly red stem of R-5 untreated and Pestalotiopsis-inoculated seedling (C).

How the R-5 strain induced phytoalexin synthesis was examined by focussing attention on the production of anthocyan red pigment, which is a kind of phytoalexin. First, rhododendron seedlings were raised in the same manner in Example 3 (3). Next, one untreated plant; one treated with the R-5 having a leaf at the upper $4^{th}$ node, on which a mycelial disk of a plant pathogen, *Pestalotiopsis sydowiana*, had been placed, as prepared in Example 5 (1); and one untreated having a leaf at the upper $3^{rd}$ node, on which a mycelial disk of *Pestalotiopsis sydowiana* had been placed, were prepared. Subsequently, these plants were raised in an incubator at 25° C. under irradiation (about 4,000 luxes, 12 hours/day) for a week. The condition of each plant is shown in FIG. 8. As shown in FIG. 8, the untreated plant (corresponding to A shown in FIG. 8) had a green stem, while the plant inoculated with the plant pathogen (corresponding to B shown in FIG. 8) had a stem whose color had changed vivid red. In addition, the untreated plant inoculated with the plant pathogen had a stem whose color had changed red somewhat.

Next, the multiplication medium from which rhodedendron seedlings was growing was treated with mycelial solution of R-5 strain by the procedure of Example 5. The treated seedlings were cultured under light at 25° C. for 12 hours. On day 2, 4, 6, 8, and 10 after culturing, the seedlings were collected, washed with ion exchange water, and then the surface was wiped with Kimwipe. One gram of each of the seedlings was dipped in 50 ml of 0.5N HCl-methanol and allowed to stand under dark conditions at 4° C. for 24 hours. Subsequently, the products were filtered with filter papers (No.1, Toyo Roshi Kaisha, Ltd.) to obtain the resulting filtrate as anthocyanin crude extracts. Anthocyanin was also extracted from untreated seedlings in the same manner. An absorbance ($A_{530}$) at 530 nm was measured for a mixture of 300 µl of 5N HCl-methanol and 100 µl of 3N HCl-methanol. This absorbance was determined as a blank. Further, 300 µl each of anthocyanin crude extracts and 100 µl of 3N HCl-methanol were mixed. Then an absorbance $A_{530}$ was also measured for these mixtures. Moreover, to decolorize anthocyanin contained in the crude extracts, 300 µl each of the anthocyanin crude extracts and 100 µl of hydrogen peroxide solution were mixed, and allowed to stand for 15 minutes. An absorbance $A_{530}$ was measured for the decolorized extracts. The absorbance measured after anthocyanin decolorization was subtracted from the absorbance before decolorization to determine an absorbance showing the amount of anthocyanin.

Figure 9:
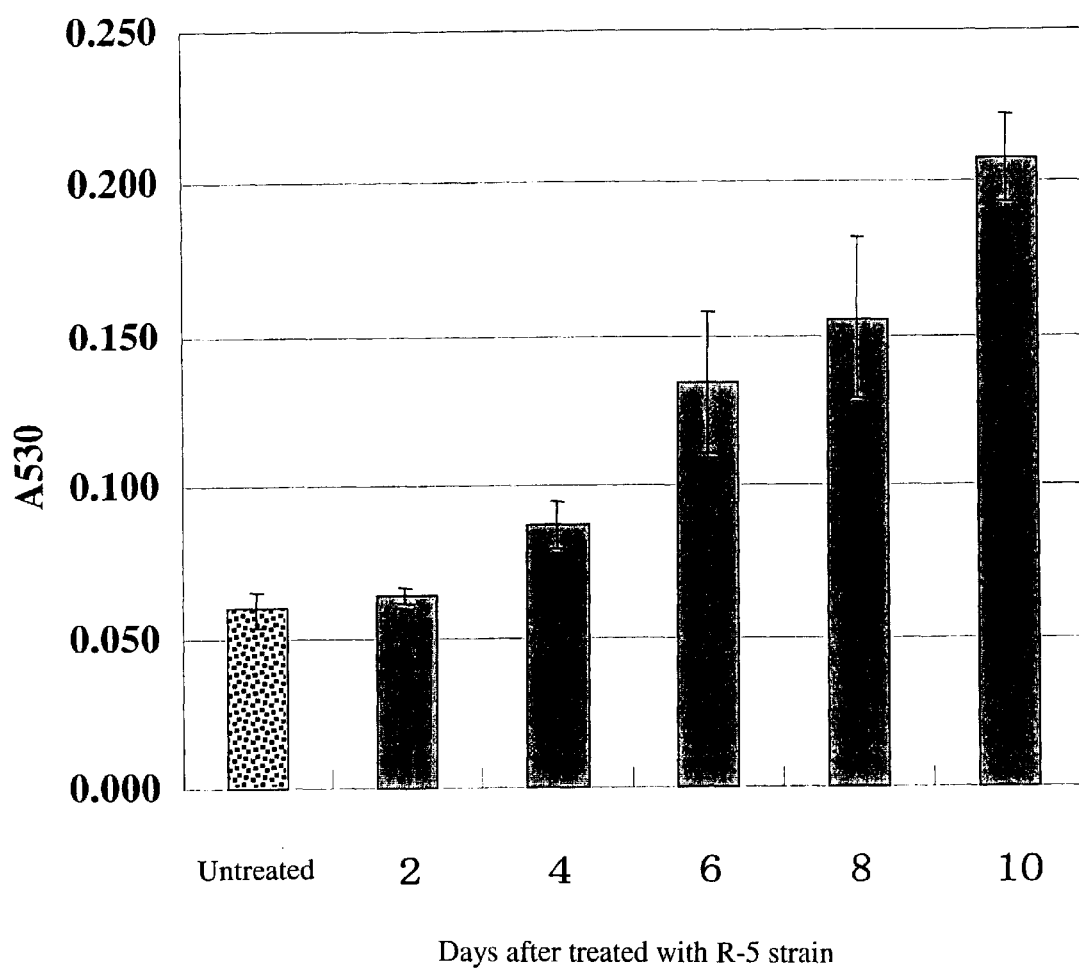
FIG. 9 is a graph showing changes with time in the amount of anthocyanin in rhododendron plants following treatment with the R-5 strain.

FIG. 9 shows the result. The absorbance $A_{530}$ showing the amount of anthocyanin contained in the untreated seedlings was approximately 0.06; in the seedlings treated with R-5 strain, the absorbance $A_{530}$ gradually increased with days and reached 0.21 on day 10, about 4-fold greater than that of the untreated seedlings. This suggests that the treatment of rhododendron seedlings with R-5 strain can induce anthocyanin (that is, phytoalexin) in rhododendron plants.

Example 8

Extraction of an Antibiotic Derived from R-5 Strain

The surfaces of multiplication medium, on which rhododendron seedlings were growing, were treated with mycelial solution of R-5 strain, and cultured under light (about 4,000 luxes, 12 hours/day) at 25° C. for 10 days. Extraction of antibiotics from 219.3 g of the multiplication medium and 12.17 g of the rhododendron seedlings was attempted. As a control, antibiotics were also extracted from 221 g of multiplication medium untreated with R-5 strain and 8 g of the seedlings in the same manner. First, R-5 strain-treated or -untreated rhododendron seedlings were pulled out from the multiplication medium were washed well with ion exchange water. Then the seedlings were frozen and crushed with pestle and mortar in liquid nitrogen. The product was transferred in a flask, and then 200 ml of methanol was added to the flask. After stirred well overnight, the product was filtrated through absorbent cotton. Hexan (about half the filtrate) was added to the filtrate. The mixture was mixed well, separated with a separating funnel, thereby collecting the methanol layer. This procedure was repeated four times to remove chlorophyll contained in the filtrate. The obtained methanol layer was evaporated to dryness with an evaporator, and the extracts on the wall were collected with ethyl acetate, followed by addition of ion exchange water and separation. An appropriate amount of sodium sulfate was added to the collected ethyl acetate layer for dehydration, and the mixture was filtrated through absorbent cotton. The filtrate was concentrated with an evaporator, eluted with acetone, and evaporated again. This procedure was repeated two times, and the resulting dry materials were weighed, followed by addition of methanol for HPLC to 1 mg (dry weight)/ml. The product was filtrated through Cosmonice Filter (Nacalai tesque, Inc., ɸ0.45 µm), and subjected to HPLC analysis [column (4.6×250 mm, Cosmosil), acetonitrile: phosphoric acid buffer =60:40, amount of injected sample 25 µl, flow velocity 1.0 ml/min].

Methanol 400 ml was added to the multiplication medium treated or untreated with R-5 strain, from which the seedlings had been pulled out, and then stirred overnight. Then the mixture was centrifuged at 8,000 rpm for 3 minutes to collect the supernatant. The supernatant was concentrated with a rotary evaporator, and freeze-dried. Ion exchange water and ethyl acetate were added to the product and stirred well. Then only the ethyl acetate layer was collected using a separating funnel. Subsequently, sodium sulfate was added for dehydration. The product was filtrated through absorbent cotton, and the collected filtrate was concentrated with a rotary evaporator. Acetone was added to the concentrate, and concentrated with a rotary evaporator. The obtained dry materials were weighed. Next, the dry materials were dissolved in methanol for HPLC to 1 mg (weight of the dry matter)/ml, filtrated through Cosmonice Filter, and subjected to HPLC analysis [column (4.6×250 mm, Cosmosil), acetonitrile: phosphoric acid buffer =60:40, amount of injected sample 25 µl, flow velociy 1.0 mg/min].

Table 12 shows the results. HPLC analysis was performed on extracts from R-5 strain-treated rhododendron seedlings and multiplication medium. Thus peaks with UV maximum absorbance 241, 427 (shoulder) and 443 nm and with the retention time of approximately 12.8 minutes were detected for both the extracts. The results were analyzed by a known antibiotic identification system, suggesting that all of them were antibiotics belonging to actinomycin. Furthermore, the concentrations detected were 24 μg/ml (water content of rhododendron) and 7 μg/ml (water content of the medium). These antibiotic concentrations are sufficient to significantly suppress the hyphal growth of *Pestalotiopsis sydowiana* MAFF No. 305755 and of *Phytophthora cinnamomi* MAFF No. 305565.

TABLE 12

Peaks corresponding to actinomycin in the extracts and their UV absorbances

| Sample | Retention Time (min) | UV Maximum Absorbance (nm) |
| --- | --- | --- |
| Actinomycin D (commercial product) | 12.3 | 242, 427 (sh)*, 444 |
| Extracts from R-5 strain-treated seedlings | 12.9 | 241, 428 (sh), 443 |
| Extracts from R-5 strain-treated media | 12.8 | 241, 427 (sh), 443 |

*sh: shoulder

Example 9

Identification of Antibiotics Produced by R-5 Strain

R-5 strain spore suspension was inoculated in IMA-2 liquid medium, and shake-cultured for 4 days at 30° C. (shaking rate: 200 rpm). The R-5 strain culture solution was inoculated in 100 ml of autoclaved A-3M producing medium [5 g of glucose, 20 ml of glycerol, 20 g of soluble starch, 15 g of Pharmamedia (Southern Cotton Oil Co., U.S.A), 3 g of yeast extract, 1 g of Diaion HP-20 resin (Mitsubishi Chemical Corp.), and 1,000 ml of ion exchange water], then shake-cultured for 6 days at 30° C. Acetone 100 ml was added to the culture solution, extracted by shaking for 2 hours at 30° C., and centrifuged at 3,000 rpm for 10 minutes, thereby collecting the supernatant. The supernatant was concentrated with a rotary evaporator. Then ethyl acetate was added to the concentrate. The mixture was stirred well and separated with a separating funnel into water and ethyl acetate layers. Moreover, the ethyl acetate layer was completely concentrated with an evaporator, eluted with acetone, and then completely re-concentrated with an evaporator. The concentrate was eluted by adding methanol. Then the eluate was analyzed by the known antibiotic identification system using HP-1090HPLC, as well as tested for antimicrobial activity of each of the peak fractions against *Micrococcus luteus* ATCC9341 and *Saccharomyces cerevisiae* S-100.

Table 13 shows the results. The extract from IMA-2 liquid medium, in which R-5 strain had been cultured, was analyzed by HPLC using a known antibiotic identification system. Thus, a peak with a retention time of 11 minutes (peak 1) showing antimicrobial activity against *Saccharomyces cerevisiae* was detected; and a peak with a retention time of 22.1 minutes (peak 2) against *Micrococcus luteus* ATCC9341. The UV absorbance of the peaks were analyzed. Peak 1 was shown to have characteristic maximum absorbances at approximately 310, 325, 340 and 356 nm, suggesting that this peak 1 corresponds to a polyen antifungal antibiotic. In addition the peak 2 was shown to have characteristic maximum absorbances at approximately 244, 427 (shoulder) and 443 nm, suggesting that it corresponds to an antibiotic belonging to actinomycin. Therefore, it was shown that R-5 strain produces polyen anti-fungal antibiotics and antibiotics belonging to actinomycin in IMA-1 liquid medium.

TABLE 13

Peaks corresponding to antibiotics contained in the extracts of R-5 strain culture solution and their UV absorbances

| Peak | Retention Time (min) | UV Maximum Absorbance (nm) |
| --- | --- | --- |
| Peak 1 | 11.0 | 310, 325, 340, 356 |
| Peak 2 | 22.1 | 244, 427(sh)*, 443 |

*sh: shoulder

Example 10

Antibiotic Sensitivity Test For Pathogenic Filamentous Fungi

Pathogenic filamentous fungi were tested for their sensitivity against antibiotics belonging to actinomycin and polyen anti-fungal antibiotics shown to be produced by R-5 strain. First, actinomycin D or amphotericin B (polyen anti-fungal antibiotic) was dissolved to concentrations of 0.1, 1, and 10 μg/mil in potato sucrose agar medium cooled to about 45° C., and solidified. Mycelial disks with a diameter of 6 mm, which had been stamped out from mycelial mats of *Phytophthora cinnamomi* MAFF No. 305565 or *Pestalotiopsis sydowiana* MAFF No. 305755 pre-cultured for 7 days on potato sucrose agar medium, were inoculated onto the potato sucrose agar medium solidified as described above. Each diameter of the mycelial mats was measured with time for 3 days.

Figure 10:
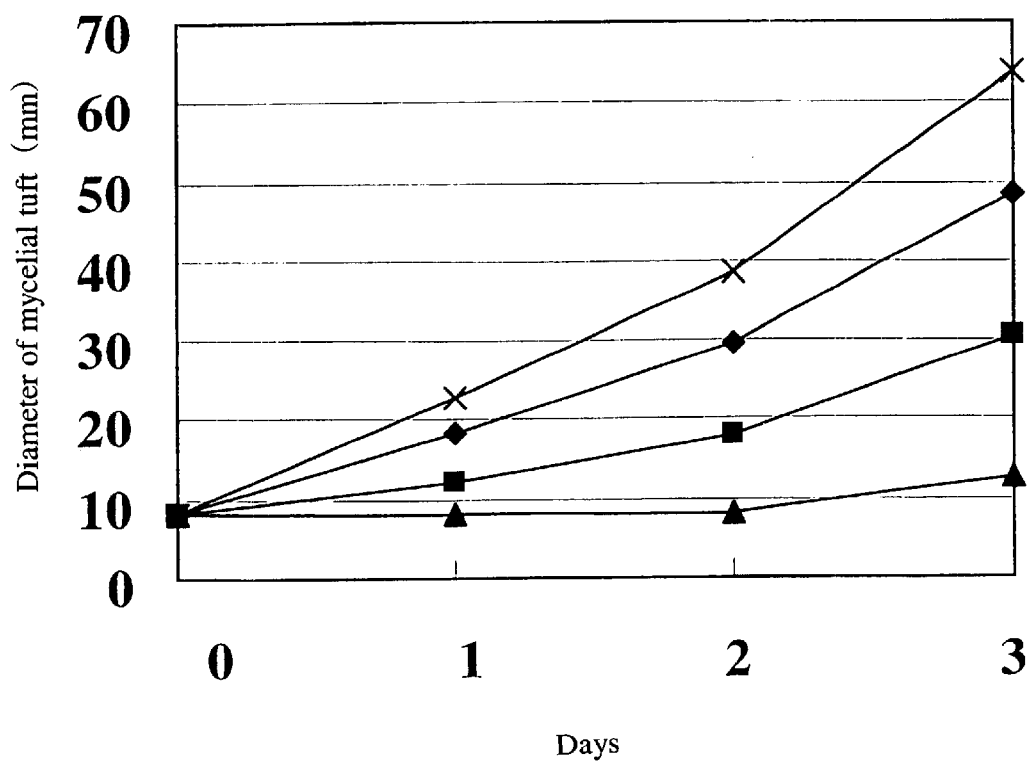
FIG. 10 is a graph showing the sensitivity of *Phytophthora cinnamomi* against actinomycin D.
Figure 11:
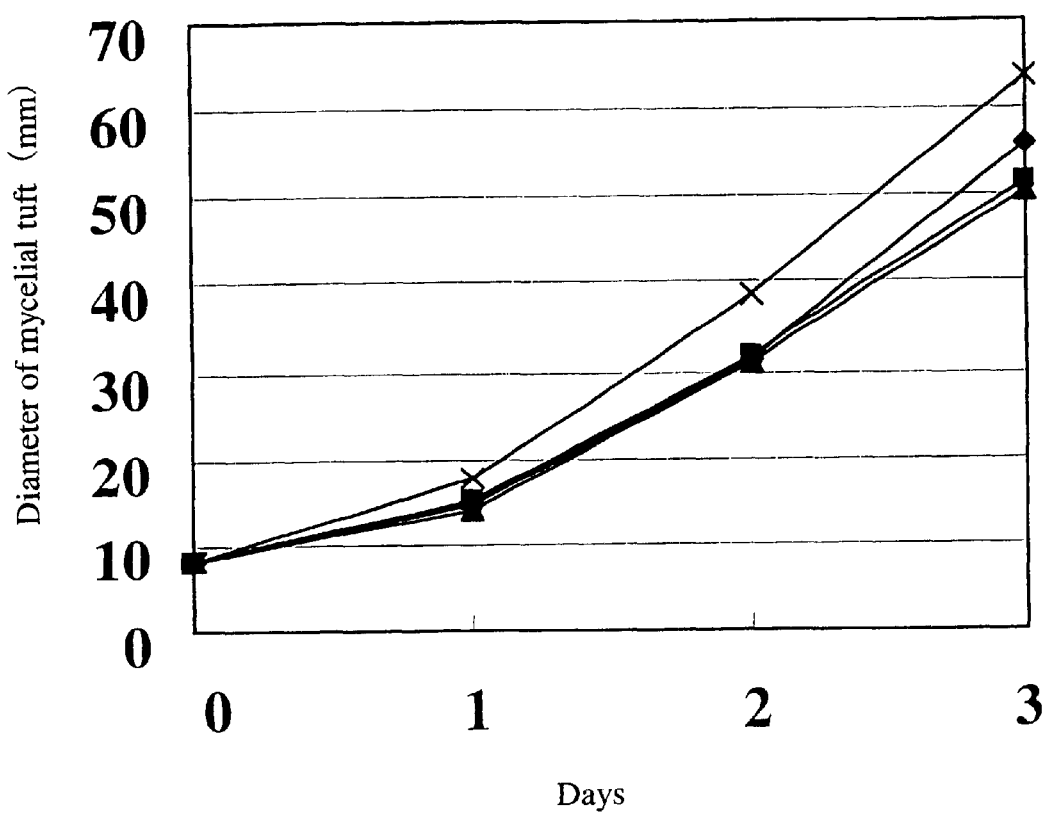
FIG. 11 is a graph showing the sensitivity of *Phytophthora cinnamomi* against amphotericin B.
Figure 12:
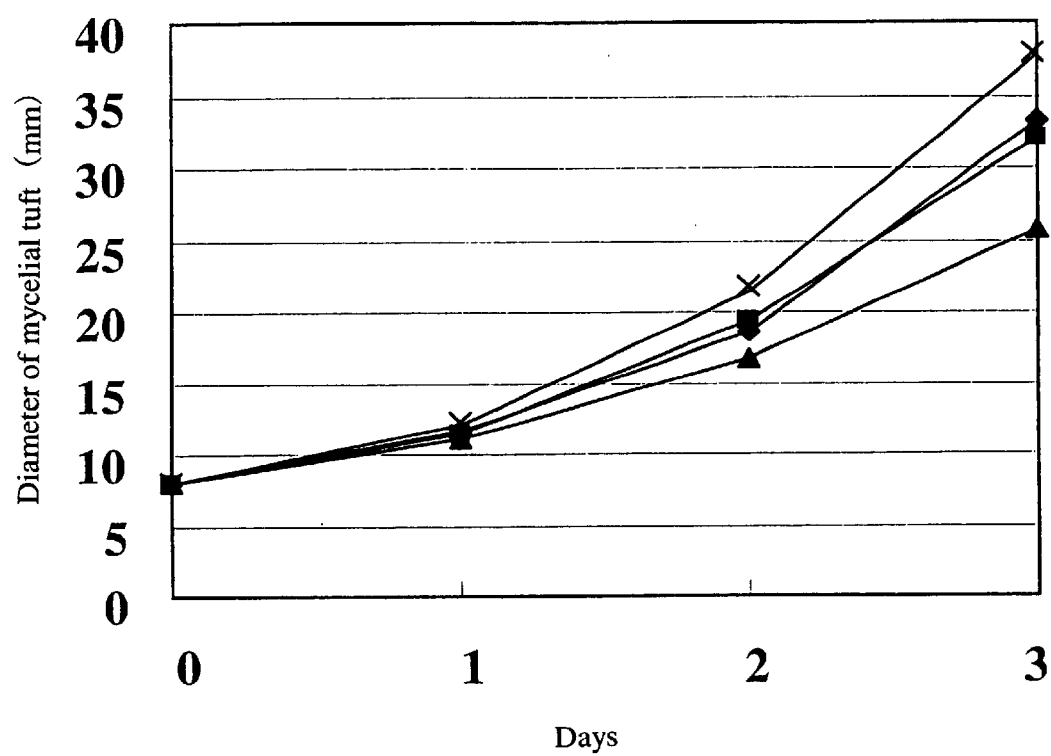
FIG. 12 is a graph showing the sensitivity of *Pestalotiopsis sydowiana* against actinomycin D.
Figure 13:
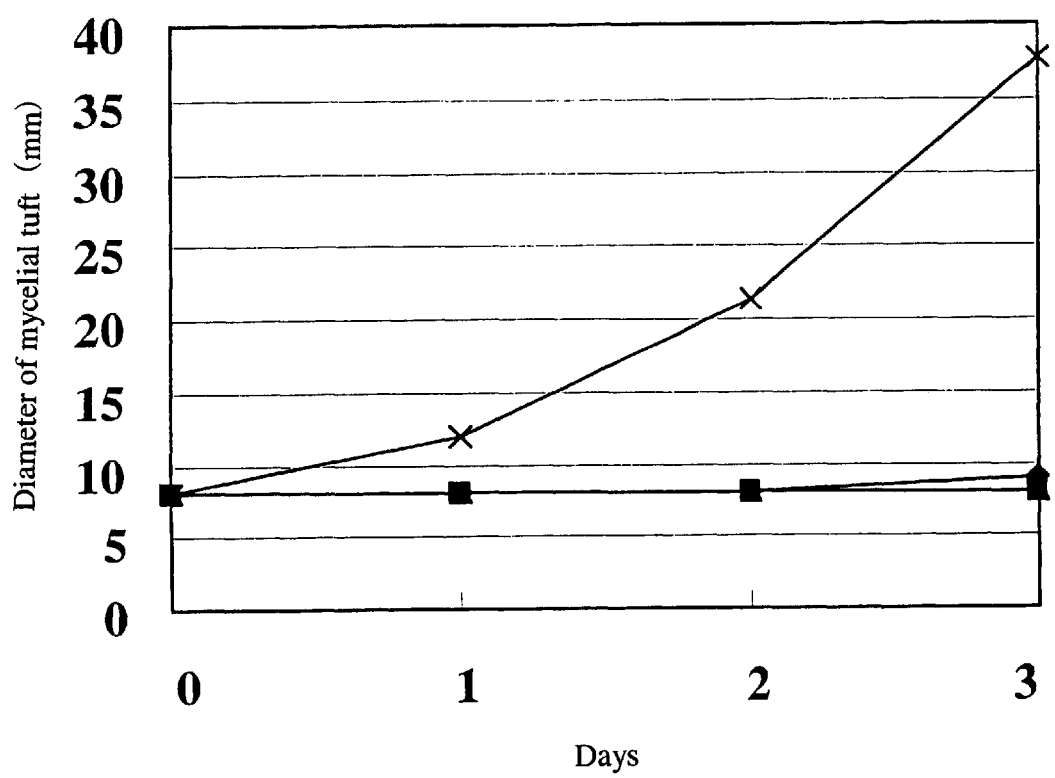
FIG. 13 is a graph showing the sensitivity of *Pestalotiopsis sydowiana* against amphotericin B.

FIGS. 10 to 13 show the results. FIG. 10 shows the sensitivity of *Phytophthora cinnamomi* against actinomycin D, FIG. 11 the sensitivity of *Phytophthora cinnamomi* against amphotericin B, FIG. 12 the sensitivity of *Pestalotiopsis sydowiana* against actinomycin D, and FIG. 13 the sensitivity of *Pestalotiopsis sydowiana* against amphotericin B. In these figures, ♦ shows 0.1 μg/ml, ■ 1 μg/ml, ▲ 10 μg/ml, and × 0 μg/ml of the concentrations of antibiotics. As shown in these figures, *Pestalotiopsis sydowiana* MAFF No. 305755 showed a high sensitivity to amphotericin B so that 0.1 μg/ml antibiotics completely suppressed the growth of the mycelia; it showed a weak sensitivity for actinomycin D, but 10 μg/ml of actinomycin D significantly suppressed the growth. On the other hand, *Phytophthora cinnamoni* MAFF No. 305565 showed almost no sensitivity to amphotericin B, but showed sensitivity to actinomycin D. The growth of the mycelial mat was suppressed by actinomycin D in concentration-dependent manner, such that the 10 μg/ml of actinomycin D completely stopped the growth.

Example 11

Assay of Antimicrobial Activity of R-5-producing Secondary Metabolic Product

R-5 strain spore suspension was inoculated in IMA-2 liquid medium, and shake-cultured (×200 rpm) for 4 days at 30° C. The R-5 strain culture solution was inoculated in 100 ml of autoclaved A-3M producing medium [5 g of glucose, 20 ml of glycerol, 20 g of soluble starch, 15 g of Pharma media (Southern Cotton Oil Co., U.S.A), 3 g of yeast extract, 1 g of Diaion HP-20 resin (Mitsubishi Chemical Corp.), and 1,000 ml of ion exchange water], then shake-cultured for 6 days at 30° C. Acetone 100 ml was added to the culture solution, extracted by shaking for 2 hours at 30° C., and centrifuged at 3,000 rpm for 10 minutes, thereby collecting the supernatant. Filter disks (a diameter of 5 mm) immersed in the supernatant of the extract was air-dried in a clean bench. Then the filter disks were separately placed on bacteria, yeast and filamentous fungi plates, and cultured over night at 37° C., 30° C., and 25° C., respectively. Diameters of growth inhibition zones appeared around the peripheries of the filter disks were measured. Various bacteria, yeast and filamentous fungi plates used for the assay above were prepared as follows. One ml each of four types of bacterial suspensions [*Escherichia coli* NIHJ JC-2, *Bacillus subtilis* M-45, *Staphylococcus aureus* 209P JC-1 or *Micrococcus luteus* ATCC 9341 had been suspended in sterilized water] was mixed well with 50 ml of nutrient agar (Difco) cooled to about 45° C. The mixtures were dispensed into Petri dishes for solidification (bacterial plate). Two types of yeast [*Candida albicans* A9540 or *Saccharomyces cerevisiae* S-100] and 7 types of filamentous fungi [*Phytophthora cinnamomi* MAFF No. 305565, *Pythium aphanidermatum* Py-3, Rhizoctoniasolani PE-75, *Fusarium avenaceum* Fu-20, *Sclerotinia homoeocarpa* Sc-8, *Botrytis cinerea* MAFF No. 410083, or *Pestalotiopsis sydowiana* MAFF No. 305755] were separately inoculated in potato dextrose broth (Difco) and shake-cultured at 200 rpm for 3 days at 25° C. The filamentous fungi were ground after culturing. Thus-obtained yeast culture solution or ground filamentous fungi 1 ml was mixed well with 50 ml of a potato sucrose agar medium cooled to about 45° C., dispensed into a Petri dish, allowed to solidify to prepare yeast and filamentous fungi plates.

Table 14 shows the results. As a result of assay of the antimicrobial activity, growth inhibition zones with a diameter of 28 to 39 mm were formed against a Gram positive bacteria, *Bacillus subtilis* M-45, *Staphylococcus aureus* 209P, and *Micrococcus luteus* ATCC 9341, but no activity was shown against Gram negative bacterium *Escherichia coli* NIHJ JC-2. For both the yeast strains, *Candida albicans* A9540 and *Saccharomyces cerevisiae* S-100, growth inhibition zones with a diameter of 25 mm were formed. Furthermore, growth inhibition zones with a diameter of 30 mm or more were formed against all of the sample pathogenic filamentous fungi including *Phytophthora cinnamomi* MAFF No. 305565 and *Pythium aphanidermatum* Py-3, both belonging to Mastigomycetes, *Botrytis cinerea* MAFF No. 410083 belonging to Deuteromycotina (Ascomycotina if the perfect stage was present), *Fusarium avenaceum* Fu-20 (Ascomycotina if the perfect stage was present), *Rhizoctonia solani* PE-75 (Basidiomycotina if the perfect stage was present), and *Pestalotiopsis sydowiana* MAFF No. 305755 and *Sclerotinia homoeocarpa* Sc-8 belonging to Ascomycotina. These results suggest that the antibiotics produced by R-5 strain in IMA-1 medium shows antimicrobial activity against a wide variety of microbial species including Gram-positive bacteria, yeast, and filamentous fungi.

TABLE 14

Antimicrobial activity spectrum of acetone extracts of R-5 strain culture broth

| | Sample bacteria/yeast/filamentous fungi | Diameter of Growth Inhibition Zone (mm) |
|---|---|---|
| Bacteria | *Escherichia coli* NIHJ JC-2 | 0 |
| | *Bacillus subtilis* M-45 | 39 |
| | *Staphylococcus aureus* 209P JC-1 | 28 |
| | *Micrococcus luteus* ATCC9341 | 30 |
| Yeast | *Candida albicans* A9540 | 25 |
| | *Saccharomyces cerevisiae* S-100 | 24 |
| Pathogenic filamentous fungi | *Phytophthora cinnamomi* MAFF No. 305565 | 30 |
| | *Pestalotiopsis sydowiana* MAFF No. 305755 | 40 |
| | *Botrytis cinerea* MAFF No. 410083 | 40 |
| | *Sclerotinia homoeocarpa* Sc-8 | 45 |
| | *Fusarium avenaceum* Fu-20 | 32 |
| | *Rhizoctonia solani* PE-75 | 40 |
| | *Pythium aphanidermatum* Py-3 | 32 |

The present invention provides Streptomyces sp. R-5 strain; a plant disease control agent containing the strain as an active ingredient; a method for producing disease-resistant plants comprising inoculating the strain to plants; and a phytoalexin inducer agent containing the strain as an active ingredient.

This specification includes part or all of the contents as described in the specification and/or drawings of Japanese Patent Application No. 2000-65511 and No. 2001-9323, which are priority documents of the present application.

What is claimed is:

1. A method for producing a disease-resistant plant comprising inoculating Streptomyces sp. R-5 to the plant.

2. The production method of claim 1 wherein Streptomyces sp. R-5 is Streptomyces sp. FERM BP-7179.

3. The production method of claim 1, wherein the plant is a seedling.

4. A method for producing disease-resistant plants, comprising inoculating the plant with Streptomyces sp. R-5, wherein the plant belongs to the family Ericaceae.

5. The production method of claim 4 wherein the plant belonging to the family Ericaceae is either rhododendron or mountain laurel.

6. A method for producing disease-resistant plants comprising inoculating Streptomyces sp. R-5 to a tissue culture medium.

7. The production method of claim 6 wherein Streptomyces sp. R-5 is Streptomyces sp. FERM BP-7179.

8. The production method of claim 6 wherein the plant is a seedling.

9. A method for producing disease-resistant plants, comprising inoculating a tissue culture medium with Streptomyces sp. R-5, wherein the plants belong to the family Ericaceae.

10. The production method of claim 9, wherein the plants belonging to the family Ericaceae is either rhododendron or mountain laurel.

* * * * *